United States Patent [19]

Ruehl et al.

[11] Patent Number: 5,192,808

[45] Date of Patent: Mar. 9, 1993

[54] THERAPEUTIC EFFECT OF L-DEPRENYL IN THE MANAGEMENT OF PITUITARY-DEPENDENT HYPERADRENOCORTICISM (CUSHING'S DISEASE)

[75] Inventors: William W. Ruehl, Overland Park; David S. Bruyette, Manhattan; David Stevens, Overland Park, all of Kans.

[73] Assignee: Deprenyl Animal Health, Inc., Overland Park, Kans.

[21] Appl. No.: 858,702

[22] Filed: Mar. 27, 1992

Related U.S. Application Data

[63] Continuation-in-part of Ser. No. 643,452, Jan. 18, 1991, which is a continuation-in-part of Ser. No. 576,011, Aug. 31, 1990, Pat. No. 5,151,449.

[51] Int. Cl.$^5$ ............................................ A61K 31/135
[52] U.S. Cl. ..................................... 514/654; 514/646
[58] Field of Search ................................. 514/654, 646

[56] References Cited

U.S. PATENT DOCUMENTS

| | | | |
|---|---|---|---|
| 4,564,706 | 1/1986 | Ecsery et al. | 564/376 |
| 4,861,800 | 8/1989 | Buyske | 514/646 |
| 4,871,550 | 10/1989 | Millman | 424/601 |
| 4,880,833 | 11/1989 | Knoll et al. | 514/565 |
| 4,916,151 | 4/1990 | Bey et al. | 514/419 |

FOREIGN PATENT DOCUMENTS

| | | |
|---|---|---|
| 871155 | 5/1971 | Canada . |
| 1215394 | 12/1986 | Canada . |

OTHER PUBLICATIONS

Milgram et al. "Maintenance on L-Deprenyl Prolongs Life in Aged Male Rats", *Life Sciences*, vol. 47, 190, pp. 415-420. (1990).

Knoll, "Extension of Life Span of Rats by Long-Term (−) Deprenyl Treatment," *The Mount Sinai Journal of Medicine*, vol. 55, No. 1, Jan. 1988, pp. 67-74.

Knoll, "The Striatal Dopamine Dependency of Life Span In Male Rats, Longevity Study with (−)Deprenyl", *Mechanisms of Ageing and Developments*, 46, (1988) 237-262.

Knoll, "The Pharmacology of Selective Mao Inhibitors", *Monoamine Oxidase Inhibitors-The State of the Art*, 1981, pp. 45-61.

Knoll, et al., "Long-Lasting, True Aphrodisiac Effect of (−)-Deprenyl in Sexually Sluggish Old Male Rats", *Modl Probl. Pharmacopsychiat.*, vol. 19, pp. 135-153 (1983).

Bice, et al., "Effect of Age on Antibody Responses after Lung Immunization", *Am. Rev. Respir. Dis.* (1985) 132:661-665.

Jones, et al., "The Effects of Aging on Pulmonary Immune Responses to Streptococcus Pneumoniae Pneumonia", *I.T.R.I. Annual Report* (1989).

Tetrud et al., "The Effect of Deprenyl (Selegiline) on the Natural History of Parkinson's Disease", *Science*, vol. 245, pp. 519-522 (1989).

The Parkinson Study Group, "Effect of Deprenyl on the Progression of Disability in Early Parkinson's Disease", *New England Journal of Medicine* 321:1364-1371 (Nov. 16), 1989.

*Primary Examiner*—Frederick E. Waddell
*Assistant Examiner*—T. J. Criares
*Attorney, Agent, or Firm*—Zarley, McKee, Thomte, Voorhees & Sease

[57] ABSTRACT

A method of treating Cushing's Disease comprising treating mammals, and especially humans, dogs, horses or ponies with from 0.01 to about 4.0 mg/kg of body weight of L-Deprenyl, preferably daily, to achieve and maintain remission.

7 Claims, No Drawings

THERAPEUTIC EFFECT OF L-DEPRENYL IN THE MANAGEMENT OF PITUITARY-DEPENDENT HYPERADRENOCORTICISM (CUSHING'S DISEASE)

CROSS REFERENCE TO RELATED APPLICATIONS

This application is a continuation-in-part of earlier filed co-pending application of Milgram, et. al., entitled "New Uses of L-deprenyl and Compositions for Same" Ser. No. 07/643,452 filed Jan. 18, 1991, pending, which itself is a continuation-in-part of earlier filed Mil et. al. U.S. application, Ser. No. 07/576,011, U.S. Pat. No. 5,151,449, entitled "Use of L-deprenyl for Retention of Specific Physiological Functions", filed Aug. 31, 1990.

BACKGROUND OF THE INVENTION

L-deprenyl is a selective monamine oxidase B (MAO-B) inhibitor, which is widely used as an adjunct in the treatment of Parkinson's disease. While it's most common usage is for the treatment of Parkinson's disease, L-deprenyl was originally developed as an antidepressant agent. Recent testing has indicated that L-deprenyl may have some effect on increasing sexual response in aging mammals, and also may have some effect, as demonstrated in laboratory rodents in increasing the natural life span. However, to date L-deprenyl has only been medically approved by regulatory agencies for use as an adjunctive treatment for Parkinson's disease.

Hyperadrenocorticism (Cushing's syndrome) is a common endocrine disorder. Currently two main subtypes of hyperadrenocorticism are recognized. Functional adrenal neoplasia accounts for about 20% of all cases of hyperadrenocorticism and represents the only form of non-ACTH dependent disease. Functional adrenal neoplasia is characterized by elevated serum cortisol concentrations, decreased plasma ACTH levels, and lack of suppression of the elevated cortisol concentration following the administration of a high dose (0.1 mg/kg) of dexamethasone (see definition of HDDS test, below).

The remainder of cases result from excessive production of ACTH. This most commonly occurs with pituitary overproduction of ACTH (pituitary-dependent hyperadrenocorticism, PDH, Cushing's disease) as the result of hyperplasia or tumor formation. This patent application refers specifically to these cases of pituitary over-production of ACTH. Finally, other cases of ACTH-dependent disease occur when tumors in other parts of the body secrete ACTH. This disorder is very uncommon. PDH is characterized by elevated serum cortisol concentrations, normal to elevated plasma ACTH concentrations, and suppression of serum cortisol concentration in response to a high dose of dexamethasone.

Several subtypes of PDH may occur. ACTH is normally produced and secreted from a portion of the pituitary called the pars distalis (PD). ACTH secretion in the PD is stimulated by corticotropin releasing hormone (CRH). ACTH can also be secreted from the pars intermedia (PI). Secretion and regulation of ACTH from the PI is under negative control by dopamine. Furthermore, experimentally induced chronic dopamine inhibition unmasks CRH stimulated release of ACTH from the PD. This implies that disease in either the PI or PD that results in increased concentrations of ACTH, may be Controlled by increasing dopamine concentrations. It has been hypothesized that dopamine depletion may therefore play a role in PDH. Excessive ACTH secretion lead to bilateral adrenal hyperplasia and results in overproduction of the steroid hormone cortisol. High levels of cortisol lead to the clinical signs that typify the disorder: excessive water drinking and urination, weight gain, a pot-bellied appearance, thinning of the skin, and progressive loss of hair. In the long term, high levels of cortisol can lead to heart disease and diabetes While therapeutic guidelines for Cushing's disease are established, these treatments generally are designed to decrease the production of cortisol by the adrenal and do nothing to address the primary problem, excessive release of ACTH by the pituitary. In addition, established therapies for Cushing's are associated with a number of serious, sometimes fatal, side-effects such as Addison's disease.

There is therefore a continuing and real need for the development of medications which can effectively treat Cushing's disease (especially in human, canine, equine species) addressing the primary problem, namely excessive release of ACTH by the pituitary and by addressing the problem in a manner of treatment which does not cause serious side effects.

While L-deprenyl is a known compound, it has never before been used at any level to treat Cushing's disease.

Like most drugs, L-deprenyl can have diverse physiological effects which are completely dependent upon the dose administered. In accordance with the present invention, L-deprenyl can be used for successful methods of treatment for Cushing's disease providing that it is used at the dosage levels mentioned herein, and providing it is administered at the periodic intervals and for the length of time mentioned herein. Obviously, when different dosages and levels of treatment are used, the results expressed herein may not be achieved. In fact, at higher doses, adverse behavioral effects may be encountered.

It is a primary objective of the present invention to provide an effective treatment for Cushing's disease.

Another primary objective of the present invention is to provide a treatment for Cushing's disease, which not only effectively treats the disease, but does so by addressing the primary cause of the disease, namely excessive release of ACTH by the pituitary.

A yet further objective of the present invention is to provide a treatment for Cushing's disease which does not have the serious side effects often associated with established therapies, such as Addison's disease.

The method and means of accomplishing each of the above as well as other primary objectives of the present invention will be apparent from the detailed description which will follow hereinafter.

SUMMARY OF THE INVENTION

The present invention relates to a process of using a known compound, L-deprenyl, in a new use for treatment of mammalian pituitary hyperadrenocorticism (Cushing's disease). A small but Cushing's disease treating effective amount of the compound is administered to the patients, preferably at a level of from 0.01 mg/kg of body weight to 4.0 mg/kg of body weight, initially daily until remission of pituitary dependent hyperadrenocorticism. After remission is induced, the dose may be reduced to a level sufficient to maintain remission.

DETAILED DESCRIPTION OF THE INVENTION

As earlier stated, the compound that is useful for the method or protocol of the present invention is a known compound, L-deprenyl. L-deprenyl has the formula (−)-N-α-dimethyl-N-2-propynylbenzene-ethanamine. It can be illustrated by the following structural formula:

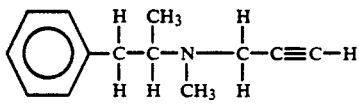

L-Deprenyl also is at times referred to as (−)deprenyl to illustrate that it is a levorotary isomer which is the active form for treatment of Parkinson's disease. Typically, it is provided in a pharmaceutically acceptable salt form thereof such as the hydrochloride salt.

As used here, pharmaceutically acceptable salt form thereof, means the following. Acceptable for use in the pharmaceutical or veterinary art, being nontoxic or otherwise not pharmaceutically or veterinary medically unacceptable "Acceptable salt form thereof" means salts formed with inorganic acids such as hydrochloric acid, hydrobromic acid, sulfuric acid, nitric acid, phosphoric acid, and the like, and as well organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, etc.

Administration of the active compound L-deprenyl to treat Cushing's disease can be via any of the accepted modes of administration for systemically active substances. These methods include oral, parenteral, IV, IM, subcutaneous and other systemic, aerosol, and topical forms, as well as sustained release systems like transdermal patches Preferably administration is oral.

The compositions of the present invention may be any of those known in the pharmaceutical and veterinary arts which are suitable for the method of administration and dosage required in any particular circumstance. In the case of both pharmaceutical and veterinary applications, such compositions may include tablets, pills, capsules, powders, aerosols, suppositories, skin patches, parenteral, and oral liquids including oil aqueous suspensions, solutions and emulsions. It may include long acting injectables and sustained release devices.

When the dosage is in solid form, solid pharmaceutical carriers such as starch, sugar, talc, mannitol, povidone, magnesium stearate, and the like may be used to form powders. Lactose and mannose are the preferred solid carrier. The powders may be used as such for direct administration to a patient or, instead, the powders may be added to suitable foods and liquids, including water, to facilitate administration.

The powders also may be used to make tablets, or to fill gelatin capsules. Suitable lubricants like magnesium stearate, binders such as gelatin, and disintegrating agents like sodium carbonate in combination with citric acid may be used to form the tablets.

Unit dosage forms such as tablets and capsules may contain any suitable predetermined amount of L-deprenyl, advisably as a nontoxic acid addition salt, and may be administered one or more at a time at regular intervals as later described. Such unit dosage forms, however, should with a broad range guideline contain a concentration of 0.01 mg/kg to 4.0 mg/kg of one or more forms of the active L-deprenyl.

A typical tablet for the specified uses mentioned herein in a 25 kg dog may have the composition.

|  | Mg. |
| --- | --- |
| 1. L-deprenyl | 25 |
| 2. Mannitol | 100 |
| 3. Stearic acid | 3 |

A granulation is made from the mannitol. The other ingredients are added to the dry granulation and then the tablets are punched.

Another tablet may have the composition:

|  | Mg. |
| --- | --- |
| 1. L-deprenyl | 25 |
| 2. Starch U.S.P. | 57 |
| 3. Lactose U.S.P. | 73 |
| 4. Talc U.S.P. | 9 |
| 5. Stearic acid | 6 |

Powders 1, 2 and 3 are slugged, then granulated, mixed with 4 and 5, and tableted.

Capsules may be prepared by filling No. 3 hard gelatin capsules with the following ingredients, thoroughly mixed:

|  | Mg. |
| --- | --- |
| 1. L-deprenyl | 25 |
| 2. Lactose U.S.P. | 200 |
| 3. Starch U.S.P. | 16 |
| 4. Talc U.S.P. | 8 |

The dose regimen is an amount to effectively treat Cushing's disease, and after remission of excessive production of ACTH, as confirmed by results of LDDS tests, the amount is reduced to an "as needed" amount to maintain remission. Generally the dose regimen is 0.01 mg/kg of body weight to 4.0 mg/kg of body weight. Initially it is given daily until remission is achieved. It is preferentially given orally an divided in one to four doses per day. After remission is induced the dose can be reduced. Generally the frequency of administration after remission can be from 1 to 7 times weekly.

While not wishing to be bound by theory of operation, it is believed that the use of L-deprenyl is effective for treatment of Cushing's disease for the following reasons. As noted earlier, most cases of hyperadrenocorticism (Cushing's syndrome) are due to excess production of ACTH by the pituitary gland, which is known as PDH or Cushing's disease.

This most commonly occurs as the result of hyperplasia or tumor formation. Other cases of Cushing's syndrome occur when tumors in the adrenal secrete cortisol or tumors in other parts of the body secrete ACTH. The latter disorder is very uncommon. PDH is characterized by elevated serum cortisol concentrations and normal to elevated plasma ACTH concentrations. Very importantly, PDH is further characterized by suppression of serum cortisol concentration in response to a high dose (0.1 mg/kg) of dexamethasone, but lack of suppression of serum cortisol concentration is response to a low dose (0.01 mg/kg) of dexamethasone.

Several subtypes of PDH may occur. ACTH is normally produced and secreted from a portion of the pituitary called the pars distalis (PD). ACTH secretion in the PD is stimulated by corticotropin releasing hormone (CRH). ACTH can also be secreted from the pars intermedia (PI). Secretion and regulation of ACTH from the PI is under negative control by dopamine. Furthermore, experimentally induced chronic dopamine inhibition unmasks CRH stimulated release of ACTH from the PD. This implies that disease in either the PI or PD that results in increased concentrations of ACTH, may be controlled by increasing dopamine concentrations. It has been hypothesized that dopamine depletion may therefore play a role in PDH. Excessive ACTH secretion leads to bilateral adrenal hyperplasia and results in overproduction of the steroid hormone cortisol. High levels of cortisol lead to the clinical signs that typify the disorder.

In patients with excessive release of ACTH secondary to dopamine depletion, administration of L-deprenyl may result in remission of disease as long a dopamine producing cells still exist with the brain. In patients that have experienced a substantial loss in dopamine producing cells, treatment with L-deprenyl will have little effect. Treatment with L-deprenyl is most effective in inducing and/or maintaining remission if administered when dopamine producing cells are still present.

Patients that respond to therapy with L-deprenyl, likely still have cells capable of producing dopamine while those that have not responded, either have no or insufficient numbers of dopamine containing cells. This explanation is based on the mechanism of action of L-deprenyl. Dopamine is metabolized by monoamine oxidases (MAO), and L-deprenyl is a specific inhibitor of MAO-B. Therefore, administration of L-deprenyl to patients with PDH may ameliorate dopamine depletion, and in turn promote normalization of pituitary ACTH regulation and secretion.

The following examples are offered to further illustrate but not limit the process and compositions of the present invention.

EXAMPLES

As published repeatedly in the medical literature, spontaneously occurring PDH in dogs is very similar to, and serves as an excellent model for, PDH in humans, ponies or horses, and other mammals. Therefore, prior to treating human PDH patients with L-deprenyl a pilot study was conducted on four pet dogs known to be suffering from Cushing's disease. The test substance was selegiline hydrochloride (L-deprenyl or Anipryl ®) which is a white or almost white powder. The test substance has been formulated into 4 lots of biscored tablets (0.1, 1.0, 5.0, 15.0 mg) by Solids R & D Manufacturing, Pharmaceutical Services, University of Iowa.

The dogs were initially examined by a veterinarian and in each case a diagnosis of Cushing's disease was made (and, importantly, the presence of an adrenal tumor was ruled out) on the basis of clinical and laboratory findings, including results of the LDDS, HDDS and ACTH tests described below.

Dogs were administered orally, once daily, the earlier described tablets of L-deprenyl corresponding to a body dose of 2 mg/kg of body weight. Blood was drawn from the animals and they were tested on the days specified in the table below. The effect of the L-deprenyl treatment on the Cushing's disease was determined by using the standard evaluating test procedure with LDDS (low dose dexamethasone suppression). This is the standard test used to diagnose Cushing's disease, and to monitor therapy with L-deprenyl. The test was run according to the following described procedure.

Low Dose Dexamethasone Suppression Test (LDDS): Serum Cortisol Concentration wa determined 8 hours post the intravenous administration of 0.01 mg/kg of dexamethasone sodium phosphate. A post low-dose dexamethasone serum cortisol concentration of >28 nmol/L is diagnostic of hyperadrenocorticism. Levels of 28 or lower indicate remission of production of excess ACTH, and therefore remission of Cushing's disease. Tests Used to Differentiate PDH From Functional Adrenal Neoplasia are as follows.

Plasma ACTH Concentration: Normal reference range 20-100 ng/L. Values >40 ng/L are diagnostic for PDH when they occur simultaneously with hypercortisolemia. Although a plasma concentration of between 40 and 100 ng/L falls within the reference range for normal dogs, it is inappropriately elevated in the face of hypercortisolemia and therefore indicates ACTH dependent (pituitary) disease. Concentrations between 20 and 40 ng/L are inconclusive and values less than 20 are diagnostic for functional adrenal neoplasia.

High Dose Dexamethasone Suppression Test (HDDS). Serum cortisol concentration was determined 8 hours following the intravenous administration of 0.1 mg/kg of dexamethasone sodium phosphate. A 50% or greater reduction in the 8 hour post serum cortisol concentration is diagnostic for PDH.

The pilot study LDDS test results for the four pilot study dogs are set forth in Table 1.

TABLE 1

| Identification | Pre-L-deprenyl | Day 17 | Day 31 | Day 110 | Day 130 |
|---|---|---|---|---|---|
| BT | 143,63 | 100 | 38 | 24 | 10 |
| MT | 355,53 | 127 | 167 | * | * |
| CN | 125,165 | 13 | 6 | ** | ** |
| PF | 135,118 | 134 | 133 | * | * |

*removed from study.
**see text.

Each of the data entries represents the plasma cortisol concentration after administration of a low dose of dexamethasone, as described above. The data in the column labelled "PreDeprenyl" represent 2 independent LDDS tests performed on each patient prior to initiation of therapy with L-deprenyl, and because they exceed 28 nmol/L they confirm that each of the dogs suffered from Cushing's disease prior to the time therapy was initiated. The entries in the other columns represent results of LDDS tests after L-deprenyl was first administered, including days 17, 31, 110 and 130.

With regard to patient BT, the LDDS test results for days 110 and 130 confirm that L-deprenyl treatment resulted in Cushing's disease remission. The response of patient CN was even more rapid, with the results of LDDS tests on days 17 and 31 (13,6) being within the normal range. Further studies on patient CN provide particularly strong evidence for the efficacy of L-deprenyl in the treatment of Cushing's disease. Subsequent to achieving remission of the PDH, administration of L-deprenyl to this patient was stopped intentionally. Results of LDDS tests performed 7 and 16 days after cessation of L-deprenyl therapy were both abnormal (75, 37), confirming that when the drug was withdrawn the patient relapsed. Then, L-deprenyl therapy was REINITIATED. Fifteen days later, the LDDS test result was 17, within the normal range. Therefore, L-deprenyl is effective in inducing remission of PDH, and the effects of the drug in this disease are reversible. Furthermore, once remission is achieved, continued treatment with L-deprenyl is necessary to maintain remission.

Two dogs (MT, PF) did not respond to L-deprenyl treatment. As previously stated, this failure to respond is likely due to the lack of a sufficient number of live, dopamine-containing cells in these patients; perhaps the PDH was more severe or further progressed in these individuals. Thus, 2 of the 4 dogs in this pilot study (BT and CN) responded very well to L-deprenyl therapy, with their LDDS test results returning to within normal range, indicating therapeutic effectiveness in Cushing's disease treatment.

It therefore can be seen that the invention accomplishes at least all of its stated objectives.

What is claimed is:

1. A method of treating Cushing's disease, said method comprising:
    administering a small but Cushing's disease treating effective amount of the compound L-deprenyl, or a biologically active salt form thereof, to an affected individual for a time sufficient to result in remission of Cushing's disease.
2. The method of claim 1 wherein the dose is from 0.01 mg/kg of body weight to about 4.0 mg/kg of body weight, given daily until remission of Cushing's disease occurs.
3. The method of claim 2 wherein dosage is oral, with from 1 to 4 doses given per day.
4. The method of claim 1 wherein after remission occurs, L-deprenyl is administered for from 1 to 7 times weekly on an as needed basis to maintain the remission of Cushing's disease.
5. The method of claim 1 wherein the treated individual is a human being.
6. The method of claim 1 wherein the treated individual is a dog.
7. The method of claim 1 wherein the treated individual is a horse or pony.

* * * * *

UNITED STATES PATENT AND TRADEMARK OFFICE

CERTIFICATE EXTENDING PATENT TERM
UNDER 35 U.S.C. § 156

PATENT NO.      :   5,192,808

ISSUED          :   March 9, 1993

INVENTOR(S)     :   William W. Ruehl, et al.

PATENT OWNER    :   Deprenyl Animal Health, Inc.

PRODUCT         :   Anipryl® (selegiline hydrochloride)

This is to certify that an application under 35 U.S.C. § 156 has been filed in the U.S. Patent and Trademark Office, requesting extension of the term of U.S. Patent No. 5,192,808 based upon the regulatory review of the product Anipryl® (selegiline hydrochloride) by the Food and Drug Administration. Since it appears that the requirements of the law have been met, this certificate extends the term of the patent for the period of 272 days from August 31, 2010, the original expiration date of the patent, subject to the provisions of 35 U.S.C. § 41(b), with all rights pertaining thereto as provided by 35 U.S.C. § 156(b).

I have caused the seal of the U.S. Patent and Trademark Office to be affixed this 12th day of September 2000.

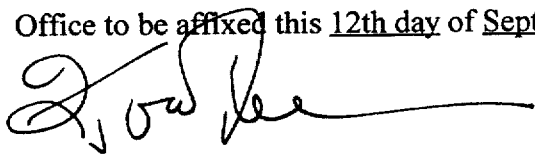

Q. Todd Dickinson
Under Secretary of Commerce for Intellectual Property
and Director of the United States Patent and
Trademark Office